(12) United States Patent
Sheanshang (10) Patent No.: US 11,498,723 B2
(45) Date of Patent: Nov. 15, 2022

(54) ENVELOPES WITH INTEGRATED EASEL FEATURES

(71) Applicant: JBM PACKAGING, Lebanon, OH (US)

(72) Inventor: Marcus Sheanshang, Lebanon, OH (US)

(73) Assignee: JBM Packaging, Lebanon, OH (US)

( * ) Notice: Subject to any disclaimer, the term of this patent is extended or adjusted under 35 U.S.C. 154(b) by 218 days.

(21) Appl. No.: 16/698,441

(22) Filed: Nov. 27, 2019

(65) Prior Publication Data

US 2020/0172295 A1 Jun. 4, 2020

Related U.S. Application Data

(60) Provisional application No. 62/777,365, filed on Nov. 30, 2018.

(51) Int. Cl.
*B65D 27/00* (2006.01)
*A61L 9/12* (2006.01)

(52) U.S. Cl.
CPC .............. *B65D 27/00* (2013.01); *A61L 9/12* (2013.01)

(58) Field of Classification Search
CPC ......... B65D 27/00; B65D 5/52; B65D 5/5206
USPC ..... 206/45.24, 45.26; 229/71, 930, 931, 237
See application file for complete search history.

(56) References Cited

U.S. PATENT DOCUMENTS

| | | | | |
|---|---|---|---|---|
| 1,454,849 A | * | 5/1923 | Ganz | B65D 5/52 206/45.25 |
| 1,563,687 A | * | 12/1925 | Chaney | A47F 5/112 248/459 |
| 1,682,963 A | * | 9/1928 | Hardy | B65D 5/5206 229/921 |
| 2,483,533 A | * | 10/1949 | Dubiner | B65D 5/4204 206/765 |
| 2,945,617 A | * | 7/1960 | Normandin | B65D 27/00 229/67.3 |
| 3,219,181 A | * | 11/1965 | Dahm | B65D 5/5246 206/45.21 |
| 4,718,545 A | * | 1/1988 | Chrzanowski | B65D 5/5266 206/45.24 |
| 5,165,649 A | * | 11/1992 | Neumann | A47B 23/044 248/459 |
| 5,351,882 A | * | 10/1994 | Krautsack | B65D 5/4208 229/164 |

(Continued)

*Primary Examiner* — Rafael A Ortiz
(74) *Attorney, Agent, or Firm* — Dinsmore & Shohl LLP (57) ABSTRACT

An envelope may include an envelope body having a first pair of substantially parallel edges that extend in a transverse direction and a second pair of substantially parallel edges that extend in a longitudinal direction, a face, and a back defining a pouch. The envelope may include a first region of the envelope body that is partially detachable from the envelope body along a line of separation to form a base support member. The envelope may further include a second region of the envelope body that is partially detachable from the envelope body along a line of separation to form a connector support member. The connector support member engages the base support member when the base support member is partially separated from the envelope body to form an easel feature in a display position. The envelope may also be incorporated into methods for displaying an envelope body.

20 Claims, 9 Drawing Sheets

(56) References Cited

U.S. PATENT DOCUMENTS

| | | | | |
|---|---|---|---|---|
| 5,788,144 | A * | 8/1998 | Sorge | A47G 1/141 |
| | | | | 229/71 |
| 7,055,692 | B2 * | 6/2006 | Waga | B65D 77/003 |
| | | | | 206/497 |
| 2006/0246265 | A1 * | 11/2006 | Rogers | B65D 27/00 |
| | | | | 428/195.1 |
| 2019/0168529 | A1 * | 6/2019 | Jones | B65D 5/5007 |

* cited by examiner

ENVELOPES WITH INTEGRATED EASEL FEATURES

CROSS-REFERENCE

This application claims the benefit of and priority to U.S. Provisional Patent Application No. 62/773,656, titled "Envelopes with Integrated Easel Features," filed Nov. 30, 2018, the details of which are hereby incorporated by reference in their entirety.

TECHNICAL FIELD

The present specification generally relates to envelopes and, more particularly, to envelopes with integrated easel features.

BACKGROUND

It is known to use envelopes for mailing or otherwise transporting letters and documents. Envelopes may be created for other purposes as well. For example, decorative envelopes may be displayed or stored in homes or businesses. Such envelopes may contain scented materials. These envelopes do not expose the scented materials directly to the surrounding air, which can diminish the rate of scent evaporation or likelihood of exposure, for example, to skin. Typically, these envelopes are laid in a drawer or are displayed on a shelf. What is needed is an envelope that can contain a scented material or other materials, such as seeds, while allowing the user the ability to display the envelope on a surface without spilling its contents.

SUMMARY

In an embodiment, an envelope includes an envelope body having a first pair of substantially parallel edges that extend in a transverse direction and a second pair of substantially parallel edges that extend in a longitudinal direction, a face, and a back defining a pouch. The envelope includes a first region of the envelope body that is partially detachable from the envelope body along a line of separation to form a base support member. The envelope further includes a second region of the envelope body that is partially detachable from the envelope body along a line of separation to form a connector support member. The connector support member engages the base support member when the base support member is partially separated from the envelope body to form an easel feature in a display configuration.

In another embodiments, an envelope includes an envelope body having a first pair of substantially parallel edges that extend in a transverse direction and a second pair of substantially parallel edges that extend in a longitudinal direction, a face, and a back defining a pouch. The envelope includes a scented material that is located within the pouch. The envelope includes a base support member partially detached from the envelope body along a line of separation and a connector support member partially detached from the envelope body along a line of separation. According to this embodiment, the connector support member is engaged with the base support member to form an easel feature in a display configuration.

In another embodiment, a method of displaying an envelope comprising an envelope body includes forming a base support member from a first region of the envelope body that is partially detachable from the envelope body along a line of separation and forming a connector support member from a second region of the envelope body that is partially detachable from the envelope body along a line of separation to form a connector support member. The envelope body has a first pair of substantially parallel edges that extend in a transverse direction and a second pair of substantially parallel edges that extend in a longitudinal direction, a face, and a back defining a pouch. The connector support member engages the base support member when the base support member is partially separated from the envelope body to form an easel feature in a display configuration.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments described herein generally relate to envelopes that include a base support member and a connector support member, thereby forming an easel once the members are moved from an initial position to a display position. The envelope may contain a scented material that can be perceived by a user from outside the envelopes. In some embodiments, the material contained in the envelope may not be a scented material, such as seeds or other materials.

Directional terms as used herein—for example up, down, right, left, front, back, top, and bottom—are made only with reference to the figures as drawn and are not intended to imply absolute orientation.

Figure 1:
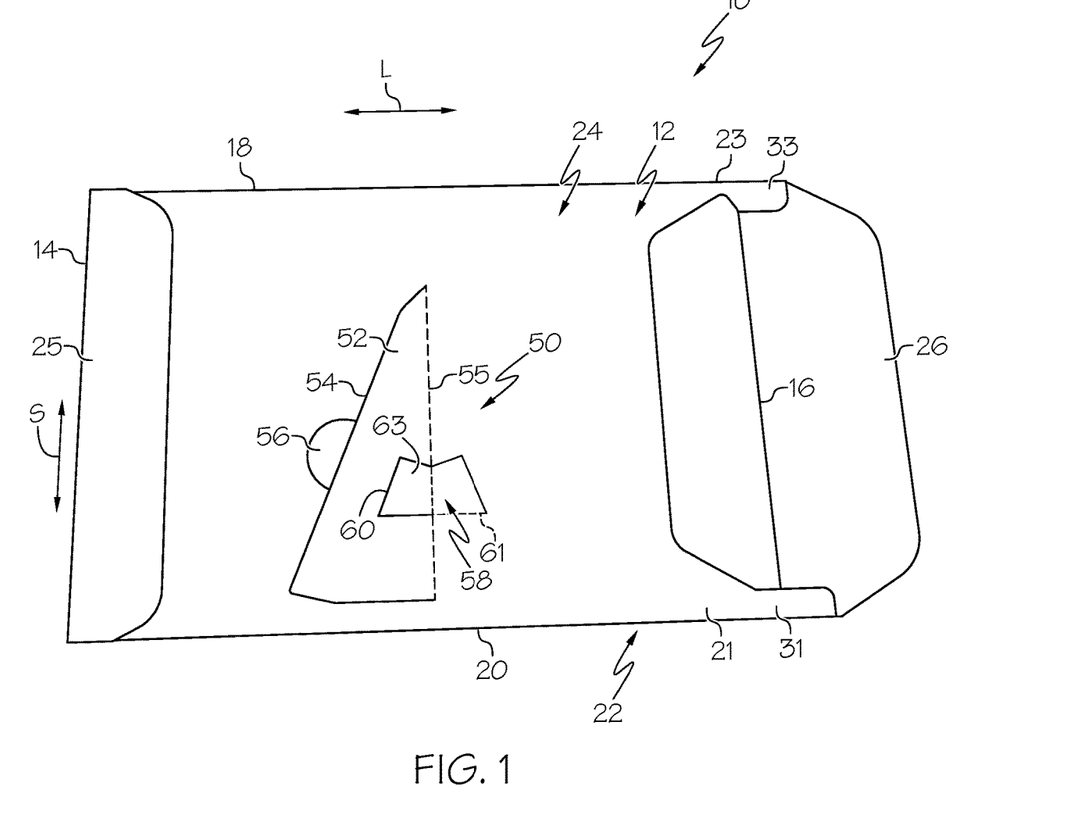
FIG. 1 is a rear view of an envelope including a base support member and a connector support member in an initial position, according to one or more embodiments described herein.

Referring to FIG. 1, an exemplary envelope 10 includes an envelope body 12 having a relatively long dimension L and a relatively short dimension S, which is perpendicular to the long dimension L. The envelope body 12 may be formed from, for example, a single sheet of material and includes a first pair of parallel edges 14 and 16 that extend in the direction of the short dimension S (sometimes referred to herein as the transverse direction) and a second pair of parallel edges 18 and 20 that extend in the direction of the long dimension L (sometimes referred to as the longitudinal direction). The edges 14, 16, 18 and 20 may be formed along scored lines that are then folded along the scored lines. While the size of dimensions L and S are illustrated as being different, they may be the same. The envelope body 12 further includes a relatively broad front side referred to herein as a face 22 and a relatively broad rear side referred to herein as a back 24. The face 22 and the back 24 extend between the edges 14, 16, 18 and 20.

Figure 1A:
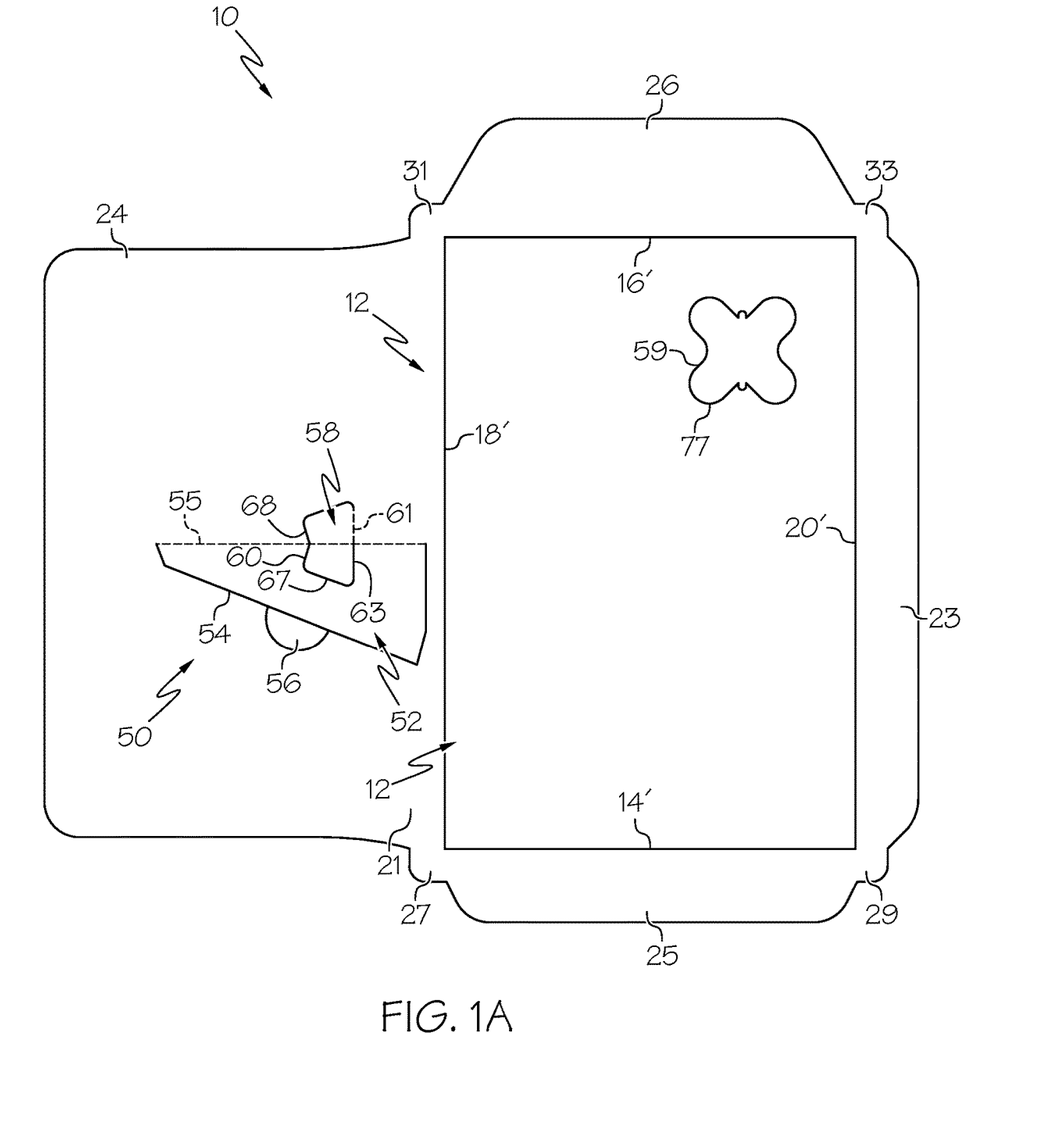
FIG. 1A is a plan view of the envelope of FIG. 1 in a flat, laid-out configuration.

Referring also to FIG. 1A, which illustrates the envelope 10 in a flat, laid-out state, the envelope 10 includes the first pair of parallel edges 14 and 16 that are formed by folds 14' and 16' and the second pair of parallel edges 18 and 20 are formed by folds 18' and 20'. As can be seen, the folds 18' and 20', once folded, provide edge flaps 21 and 23 that extend along a length of the envelope body 12. The first pair of parallel edges 14 and 16 are formed by folds 14' and 16'. Fold 14', once folded, provides an end flap 25 that extends along a width of the envelope body 12. Fold 16', once folded, provides a closure flap 26 that also extends along a width of the envelope body 12. The closure flap 26 is used to close the envelope 10 after the envelope has been filled. During assembly, the edge flap 23 is folded first and the edge flap 21 is folded next such that the back 24 overlays the edge flap 23, as can be seen in FIG. 1. Next, the end flap 25 can be folded along the fold 14', which also folds portions 27 and 29 of the edge flaps 21 and 23 forming what is known to be a "safety fold." Once the folds 14', 16' and 20' are made a partially enclosed volume is provided, which can be closed by folding the closure flap 26, which also forms a safety fold by folding portions 31 and 33.

The flaps 21, 23, 25 and 26 may include a seal adhesive or some other adhesive structure, such as an adhesive sticker, tape, glue, or combinations thereof that is used to at least partially seal the flaps 21, 23, 25 and 26 to the envelope body 12. The adhesive may be formed using gum arabic, a petroleum-based material, glue, other suitable adhesives, or combinations thereof.

In the example of FIGS. 1 and 1A, an easel feature 50 is located on the back 24 of the envelope body 12. In an initial position, the easel feature 50 lays flat against the back 24 of the envelope body 12. However, in a display position a first region of the envelope body 12, which may include, one or more base support members 52, and a second region of the envelope body 12, which may include one or more connector support members 58, are pulled away from the envelope body 12 such that the easel feature 50 supports the envelope 10 in a display position.

The base support member 52 is partially detachable from the envelope body 12 in order to form the display position. Such detachability may be due to the base support member 52 having a line of separation 54 that provides for partial separation of the base support member 52 from the back 24 of the envelope body 12. In the initial position, the line of separation 54 may be partially attached to the envelope body 12 by one or more "ticks," which are small tabs that provide resistance against detaching the base support member 52 along the line of separation 54. A bend 55 serves as a living hinge that remains attached to the envelope body 12 such that the base support member 52 remains partially attached to the envelope body 12 in the display position. An access opening 56 may be provided adjacent the base support member 52 in the initial position. A similar access opening may also be provided adjacent to the connector support member 58. The access opening 56 facilitates grasping and opening of the base support member 52 to allow the base support member 52 to be moved from the initial position, as shown in FIG. 1, to the display position, as shown in FIG. 2.

Referring still to FIGS. 1 and 1A, the easel feature 50 may further include connector support member 58. The connector support member 58 is detachable from the envelope body 12. Such detachability may be due to the connector support member 58 also having a line of separation 60, which can be seen in FIGS. 1A, 2 and 3, that provides for partial separation of the connector support member 58 from the envelope body 12. In the initial position, the line of separation 54 may be partially attached to the envelope body 12 by one or more ticks. A bend 61 serves as a living hinge that remains attached to the envelope body 12 such that the connector support member 58 remains partially attached to the envelope body 12 in the display position.

The first portion including the base support member 52 and the second portion including the connector support member 58 overlap. A section 63 of the connector support member 58 extends into and is separable from the base support member 52 in order to provide a support opening 65 (FIG. 3) through the base support member 52 once the base support member 52 is partially separated from the envelope body 12.

Figure 2:
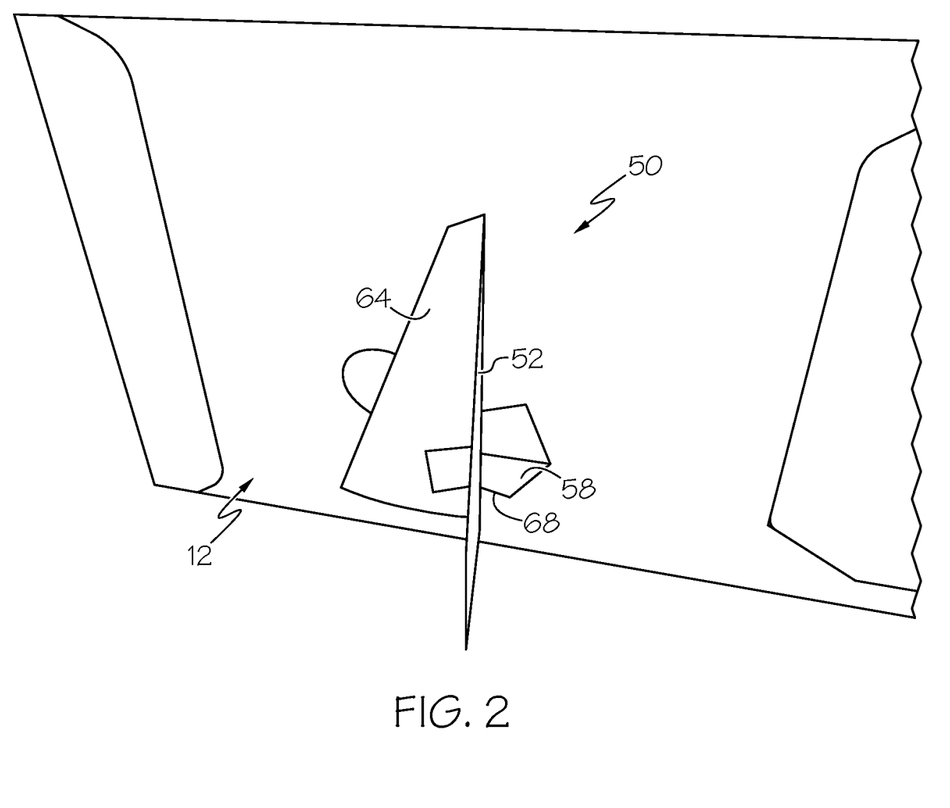
FIG. 2 is a rear view the envelope of FIG. 1, in which the base support member and the connector support member are in a display position, thereby forming an easel feature.
Figure 3:
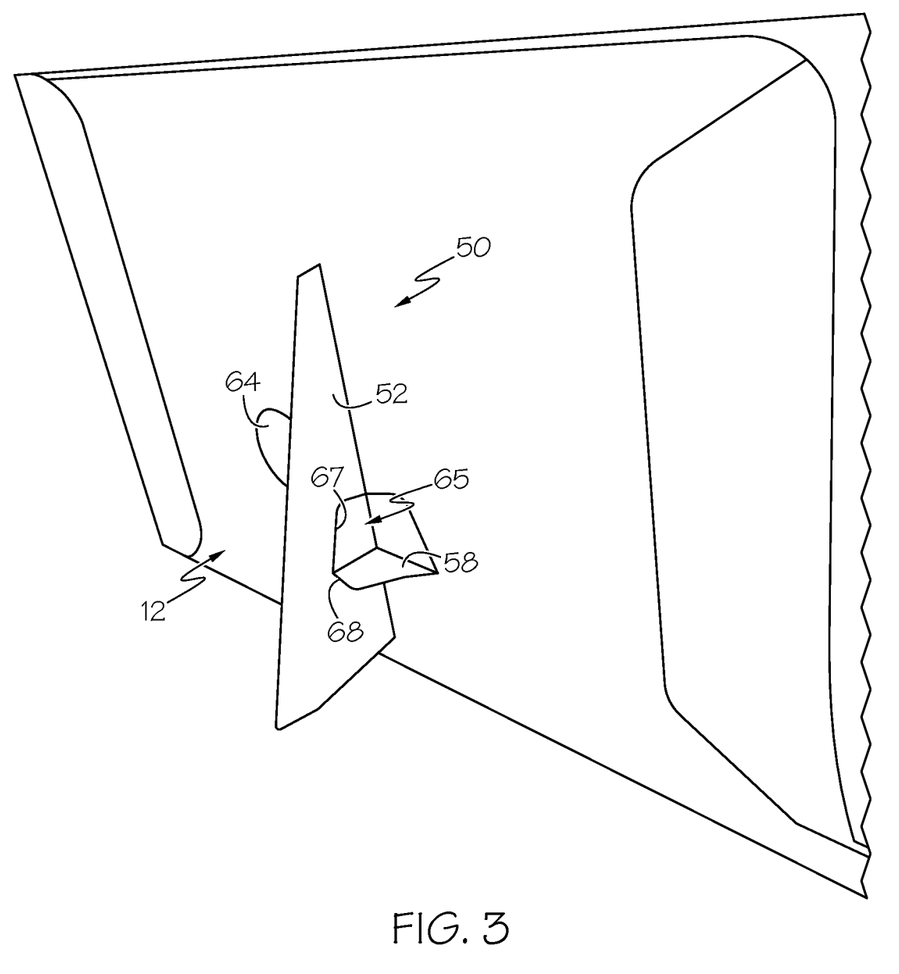
FIG. 3 is rear, perspective view of the envelope of FIG. 1, in which the base support member and the connector support member are in display position, thereby forming an easel feature.

FIGS. 2 and 3 illustrate the envelope of FIG. 1, in which the base support member 52 and the connector support member 58 are in a display position, thereby forming the easel feature 50. In order to transform the easel feature from its initial position to its display position, the base support member 52 is separated from the envelope body 12 along the line of separation 54. Then, the connector support member 58 is separated from the envelope body 12 along the line of separation 60. As can be seen, the connector support member 58 can rotate within the support opening 65 and engage a mating edge 67 of the base support member 52.

In the display position, the connector support member 58 engages the base support member 52 when the base support member 52 is partially separated from the envelope body 12. In embodiments, the connector support member 58 includes a notch 68 that engages the mating edge 67 and holds the connector support member 58 in a static position. In other embodiments, the base support member 52 includes the notch that holds the base support member 52 in a static position. The notch 68 inhibits any unwanted lateral movement of either of the support members 52 or 58, such that the envelope will not spontaneously default from the display position into the initial position. Moreover, the notch 68 provides additional friction fit between the support members 52 or 58 such that the support members 52 and 58 will not slide or collapse if the envelope 10 is moved or jostled.

The base support member 52 is separated from the envelope body 12 along the line of separation 54 such that the base support member 52 can be moved to a substantially perpendicular orientation to the envelope body 12. The separation of the base support member 52 from the envelope body 12 may be facilitated by the access opening 56, as noted above. Once the base support member 52 is substantially perpendicular to the envelope body 12, the connector support member 58 may also be separated from the envelope body 12 along the line of separation 60. The connector support member 58 may be moved to a substantially perpendicular position to the envelope body 12. The base support member 52 and the connector support member 58 are now partially separated from the envelope body 12 such that the connector support member 58 engages the base support member 52 to maintain the display position.

In certain embodiments, the envelope body 12, including the base support member 52 and the connector support member 58, are formed from a single sheet of material, as can be seen by FIG. 1A. The material forming the envelope body 12 may comprise cardboard, cardstock, paper, non-paper materials or combinations thereof. The envelope body 12 can be formed from film-type materials or other non-paper based products, so long as the material is vapor permeable to permit transmission of fragrance while otherwise forming a physical barrier for the contained substances. In embodiments, the material is scent permeable/breathable or may not be scent permeable or may be a combination of both. The material may be either opaque or clear, depending on whether it is desirable that the contents of the envelope body 12 are to be seen.

In embodiments, the base support member 52 has a height that is between 20% and 80% the height of the envelope 10 in the transverse direction. According to other embodiments, the base support member 52 has a height that is between 25% and 75%, between 30% and 70%, between 35% and 65%, between 35% and 65%, or from any other suitable range between 20% and 80% the height of the envelope 10 in the transverse direction.

Referring to FIGS. 2 and 3, the envelope 10 may further include a barrier sheet 64 that becomes exposed once the easel feature 50 is in the display position. The barrier sheet 64 may inhibit unintended spilling of any contents that may be encased within the envelope 10 and, in some embodiments, may allow the contents of the envelope 10 to be viewed. The barrier sheet 64 may also be porous to allow scented air to pass therethrough and provide increased scent permeability compared to the material of the envelope body 12.

In some embodiments scented materials, such as vermiculite, potpourri, herbs and spices such as vanilla beans, cinnamon sticks, rose petals, and other fragrant items, oils, or combinations thereof may be placed in the envelopes and the envelopes can be placed into dresser drawers, cupboards, storage boxes, and other storage areas to keep contents and/or surroundings smelling fresh and clean. The scented materials could be a variety of materials, such as granulated, or gel-based, or a solid piece that is prepared with essential oil materials. Other contents may be used, such as seeds.

The barrier sheet 64 may be a scent permeable/breathable material that is sealed along an interior of the envelope body 12. The barrier may be transparent, translucent or opaque. Designs may be provided on the barrier sheet 64, including images, words, designs, logos, or combinations thereof. The envelopes 10 may be displayed using their support members. Further, providing a barrier sheet 64 can allow for viewing of the scented materials (or not), while preventing any unintended spilling of the contents from the envelope from the envelope body.

In one or more embodiments, the envelope body 12 may further include a window 59 (FIG. 1A). The window 59 may be either fully or partially detachable from the envelope body 12 via a line of separation 77, thereby exposing the barrier sheet 64. The window 59 may assist with diffusing a scent, if the envelope 10 is filled with scented contents. Moreover, the shape of the window 59 may include any shapes from geometric patterns to outlines of animals, such as insects. In some embodiment, such as the one shown, only a portion of the window 59 may be moveable. For example, the illustrated window 59 is in the form of a butterfly where only the wings are moveable and pivotally attached to a body portion.

Figure 4:
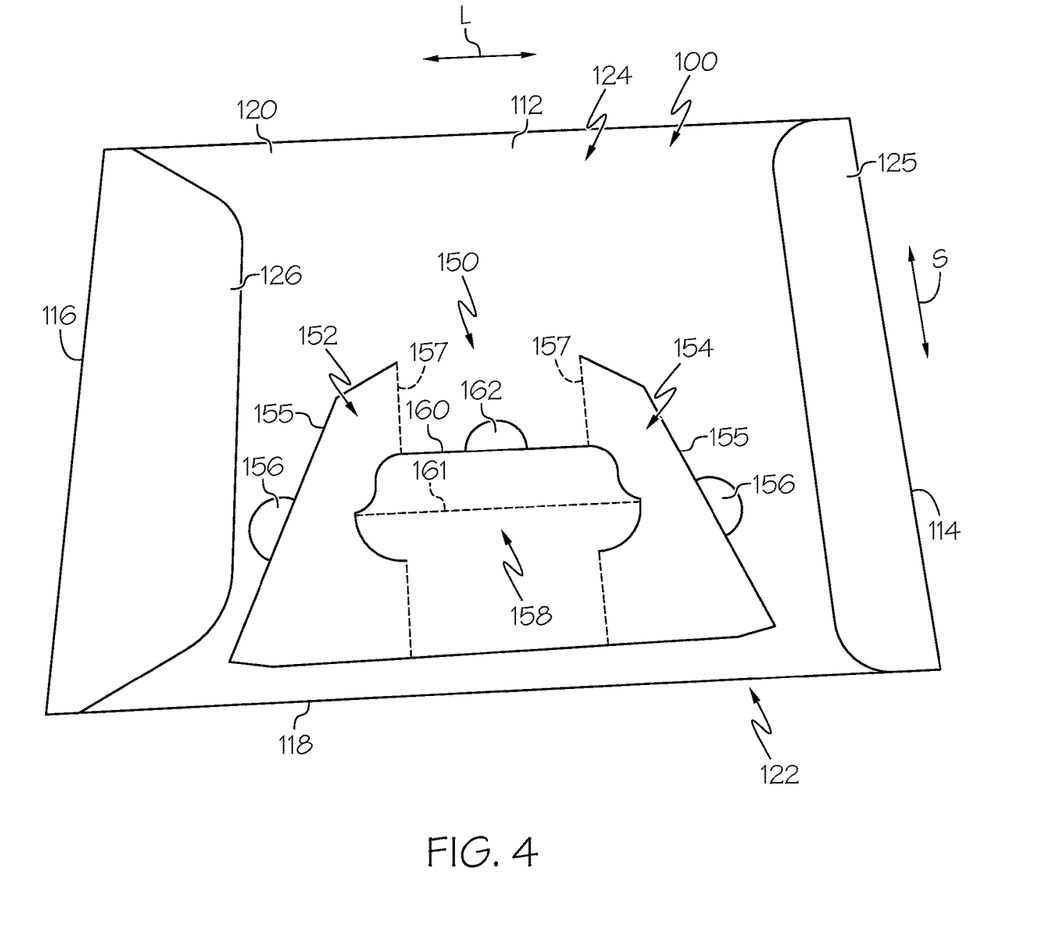
FIG. 4 is a rear view of another envelope including multiple base support members and a connector support member in an initial position, according to one or more embodiments described herein.

Referring now to FIG. 4, another envelope 100 includes an envelope body 112 having a relatively long dimension L and a relatively short dimension S, which is perpendicular to the long dimension L. The envelope body 112 may be formed from, for example, a single sheet of material and includes a first pair of parallel edges 114 and 116 that extend in the direction of the short dimension S (sometimes referred to herein as the transverse direction) and a second pair of parallel edges 118 and 120 that extend in the direction of the long dimension L (sometimes referred to as the longitudinal direction). The edges 114, 116, 118 and 120 may be formed along scored lines that are then folded along the scored lines. While the dimensions L and S are illustrated as being different, they may be the same. The envelope body 112 further includes a relatively broad front side referred to herein as a face 122 and a relatively broad rear side referred to herein as a back 124. The face 122 and the back 124 extend between the edges 114, 116, 118 and 120.

Figure 4A:
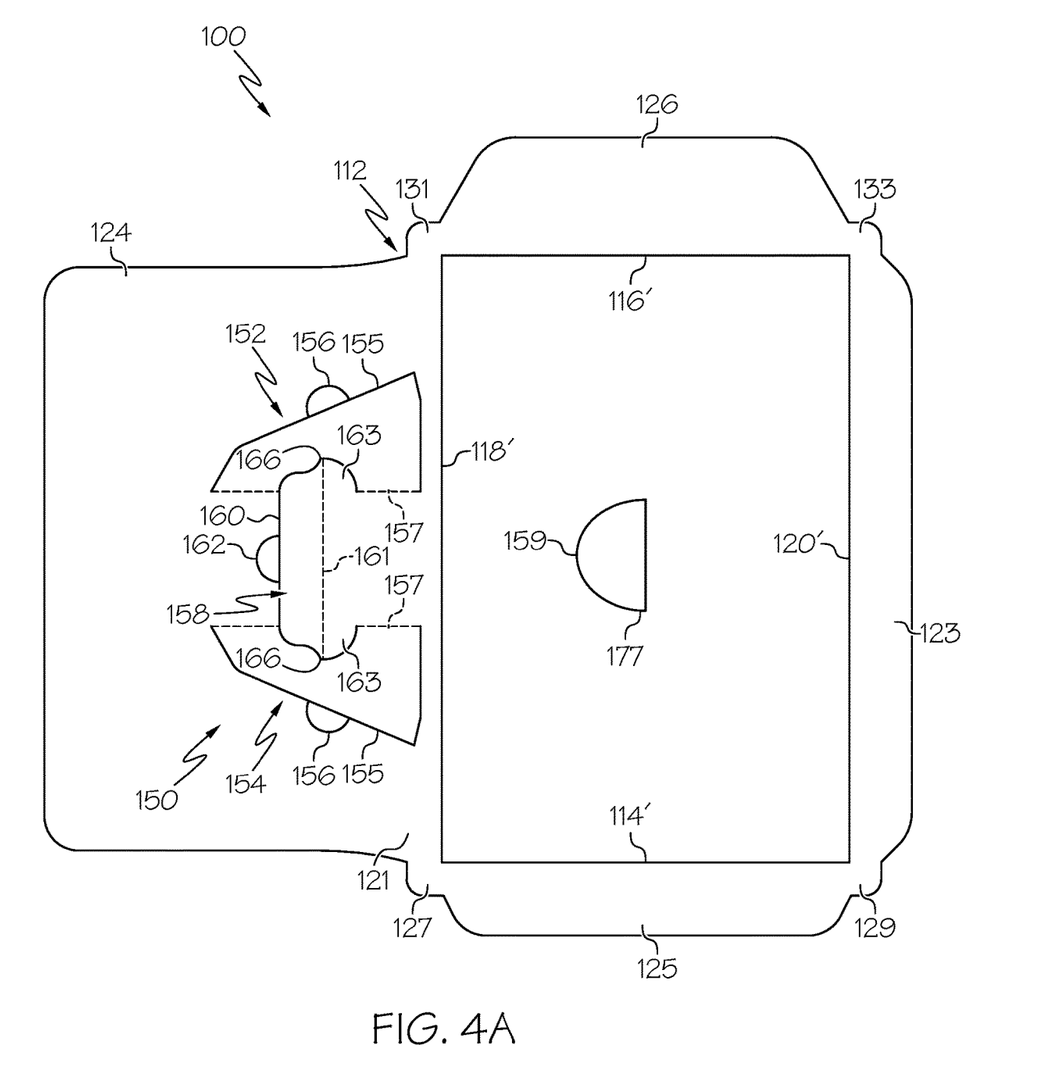
FIG. 4A is a plan view of the envelope of FIG. 4 in a flat, laid out configuration.

Referring also to FIG. 4A, which illustrates the envelope 100 in a flat, laid-out state, the envelope 100 includes the first pair of parallel edges 114 and 116 that are formed by folds 114' and 116' and the second pair of parallel edges 118 and 120 are formed by folds 118' and 120'. As can be seen, the folds 118' and 120', once folded, provide edge flaps 121 and 123 that extend along a length of the envelope body 112. The first pair of parallel edges 114 and 116 are formed by folds 114' and 116'. Fold 114', once folded, provides an end flap 125 that extends along a width of the envelope body 112. Fold 116', once folded, provides a closure flap 126 that also extends along a width of the envelope body 112. The closure flap 126 is used to close the envelope 110 after the envelope has been filled. During assembly, the edge flap 123 is folded first and the edge flap 121 is folded next such that the back 124 overlays the edge flap 123, as can be seen in FIG. 4. Next, the end flap 125 can be folded along the fold 114', which also folds portions 127 and 129 of the edge flaps 121 and 123 forming a safety fold. Once the folds 114', 116', 118' and 120' are made a partially enclosed volume is provided, which can be closed by folding the closure flap 126, which also forms a safety fold by folding portions 131 and 133.

In the example of FIGS. 4 and 4A, an easel feature 150 is located on the back 124 of the envelope body 112. In an initial position, the easel feature 150 lays flat against the back 124 of the envelope body 112. In a display position, two base support members 152 and 154 and a connector support member 158, are pulled away from the envelope body 112 such that the easel feature 150 supports the envelope 100 in a display position.

The base support members 152 and 154 are partially detachable from the envelope body 112 in order to form the display position. Such detachability may be due to the base support members 152 and 154 having a line of separation 155 that provides for partial separation of the base support members 152 and 154 from the envelope body 112. In the initial position, the line of separation 155 may be partially attached to the envelope body 112 by one or more ticks or small tabs. A bend 157 serves as a living hinge that remains attached to the envelope body 112 such that the base support members 152 and 154 remain partially attached to the envelope body 112 in the display position. An access opening 156 is provided adjacent the base support members 152 and 154 in the initial position. An access opening 162 may also be adjacent to the connector support member 158. In these embodiments, the access openings 156 facilitate grasping and opening of the base support members 152 and 154 to allow the base support members 152 and 154 to be moved from the initial position, as shown in FIG. 4, to the display position, as shown in FIG. 5.

The easel feature 150 may further include connector support member 158. The connector support member 158 is detachable from the envelope body 112. Such detachability may be due to the connector support member 158 also having a line of separation 160, which can be seen in FIG. 4A, that provides for partial separation of the connector support member 158 from the envelope body 112. In the initial position, the line of separation 154 may be partially attached to the envelope body 112 by one or more ticks or small tabs. A bend 161 serves as a living hinge that remains attached to the envelope body 112 such that the connector support member 158 remains partially attached to the envelope body 112 in the display position.

The base support members 152 and 154 and the connector support member 158 overlap. A flap section 163 of the connector support member 158 extends into and is separable from the base support members 152 and 154 in order to provide a support opening 165 (FIG. 5) through the base support member 152 once the base support member 152 is partially separated from the envelope body 112.

Figure 5:
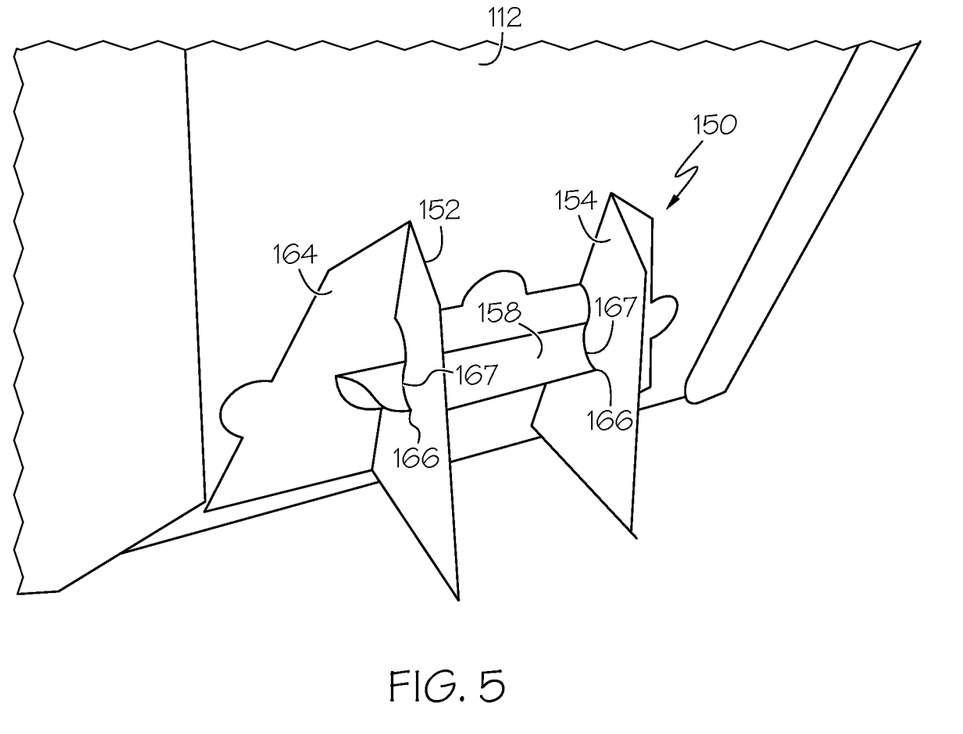
FIG. 5 illustrates the envelope of FIG. 4, in which the base support members and the connector support member are in a display position, thereby forming an easel feature.

FIG. 5 illustrates the envelope of FIG. 4, in which the base support members 152 and 154 and the connector support member 158 are in a display position, thereby forming the easel feature 150. In order to transform the easel feature from its initial position to its display position, the base support members 152 and 154 are separated from the envelope body 112 along the line of separation 155 and 171. Then, the connector support member 158 is separated from the envelope body 112 along the line of separation 160. As can be seen, the connector support member 158 can rotate within the support opening 165 and engage mating edges 167 of the base support members 152 and 154.

In the display position, the connector support member 158 engages the base support members 152 and 154 when the base support members 152 and 154 are partially separated from the envelope body 112. In embodiments, the base support members 152 and 154 includes a notch 166 that engages the mating edge 167 and holds the connector support member 158 in a static position. In other embodiments, the connector support member 158 may include the notch. The notch 166 inhibits any unwanted lateral movement of either of the support members 152 or 154, such that the envelope 110 will not default from the display position into the initial position. Moreover, the notch 166 provides additional friction fit to the support members 152, 154 and 158 such that the support members will not slide or collapse if the envelope 100 is moved or jostled.

The base support members 152 and 154 are separated from the envelope body 112 along the line of separation 155 and 171 such that the base support members 152 and 154 are substantially perpendicular to the envelope body 112. The separation of the base support members 152 and 154 from the envelope body 112 may be facilitated by the access openings 156. Once the base support members 152 and 154 are substantially perpendicular to the envelope body 112, the connector support member 158 may also be separated from the envelope body 112 along the line of separation 160. The connector support member 158 is moved to a substantially perpendicular position to the envelope body 112. The base support members 152 and 154 and the connector support member 158 are now partially separated from the envelope body 112 such that the connector support member 158 engages the base support members 152 and 154 to maintain the display position.

As above, the envelope 100 may further include a barrier sheet 164 that becomes exposed once the easel feature 150 is in the display position. The barrier sheet 164 may inhibit unintended spilling of any contents that may be encased within the envelope 100 and, in some embodiments, may allow the contents of the envelope 100 to be viewed. The barrier sheet 164 may also be porous to allow scented air to pass therethrough.

In one or more embodiments, the envelope body 112 may further include a window 159 (FIG. 4A). The window 159 may be either fully or partially detachable from the envelope body 112 via a line of separation 177, thereby exposing the barrier sheet 164. The window 159 may assist with diffusing a scent, if the envelope 100 is filled with scented contents. Multiple windows may be provided of the same or different sizes to allow some control of scent escape from the envelope body 112. Moreover, the shape of the window 159 may include any shapes from geometric patterns to outlines of animals, such as insects.

Figure 6:
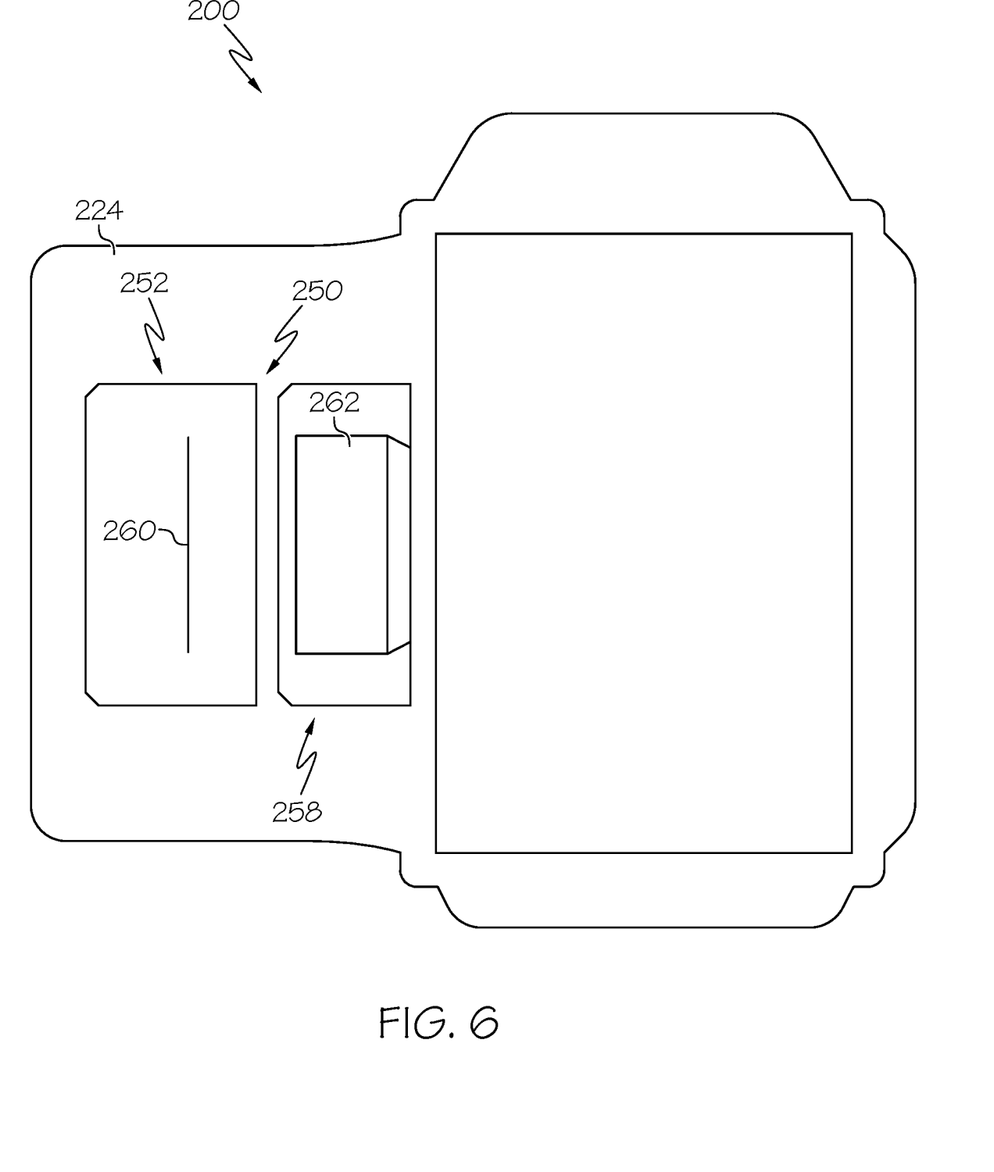
FIG. 6 is a plan view of another envelope including a square easel feature, according to one or more embodiments shown and described herein.

Referring to FIG. 6, another embodiment of an envelope 200 includes many of the elements described above with an easel feature 250 that is located on a back 224 of an envelope body 212. In an initial position, the easel feature 250 lays flat against the back 224 of the envelope body 212. In a display position, a first region of the envelope body 212 includes a base support member 252, and a second region of the envelope body 212 includes a connector support member 258, which may be pulled away from the envelope body 212 such that the easel feature 250 supports the envelope 200 in a display position.

In this embodiment, the base support member 252 includes a slot 260 that is sized to receive a support flap 262 provided by the connector support member 258. To this end, the support flap 262 can be used to hold the base support member 252 in a display configuration.

Envelopes with easel features are described herein that can stand using the easel features, which can avoid the envelopes from lying flat on an underlying furniture surface on which the envelopes are placed. Issues may be presented where envelopes with certain materials are placed flat directly on the underlying surfaces in that the essence of a fragrance can create spots or leave marks on the finish of furniture, in some instances. There may be direct contact through the envelope body between the furniture and the scented material, such as where the envelope is pressed onto the furniture. In a standing position using the easel features, there may be less contact area between the envelope body and the furniture than in a flat position, which can reduce the likelihood of interaction between the support surface and the scented materials.

Figure 7:
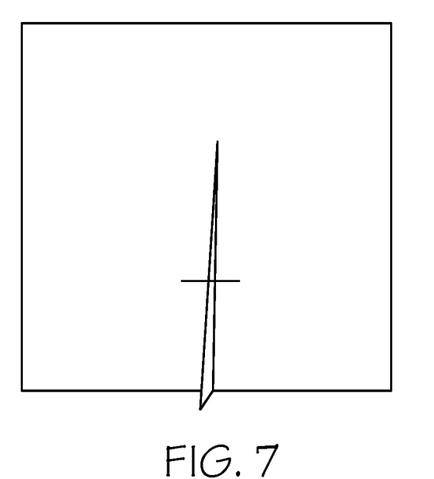
FIG. 7 is a rear view of another envelope having a square shape, according to one or more embodiments shown and described herein.
Figure 8:
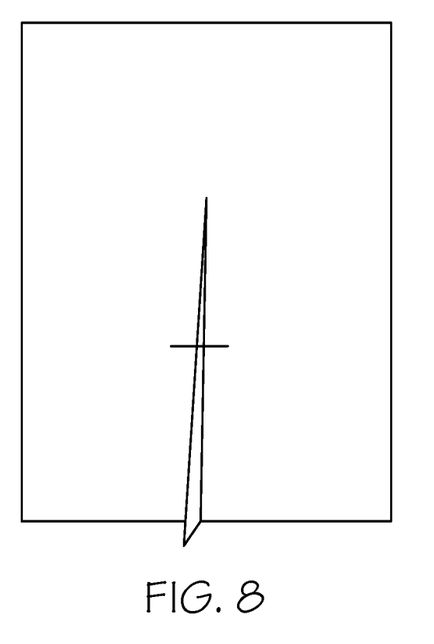
FIG. 8 is a rear view of another envelope having a rectangular shape, according to one or more embodiment shown and described herein.

While many of the above embodiments illustrate the envelopes standing with their easel features in horizontal positions (i.e., with their long sides against the support surface), the envelopes may have easel features where the envelopes stand in vertical orientations (e.g., with their short sides against the support surface and in FIG. 8). Further, referring to FIG. 7, square envelopes where the sides are the same length may be used.

It is noted that terms like "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

According to a first aspect of the present disclosure, an envelope includes an envelope body having a first pair of substantially parallel edges that extend in a transverse direction and a second pair of substantially parallel edges that extend in a longitudinal direction, a face, and a back defining a pouch. The envelope includes a first region of the envelope body that is partially detachable from the envelope body along a line of separation to form a base support member. The envelope further includes a second region of the envelope body that is partially detachable from the envelope body along a line of separation to form a connector support member. The connector support member engages the base support member when the base support member is partially separated from the envelope body to form an easel feature in a display configuration.

A second aspect of the present disclosure may include the first aspect, wherein the first region of the envelope body extends into the second region of the envelope body to provide the base support member with a support opening when the base support member is detached from the second region.

A third aspect of the present disclosure may include the first aspect or second aspect, wherein the connector support member engages a mating edge of the base support member with the easel feature in the display configuration.

A fourth aspect of the present disclosure may include any of the first through third aspects, wherein the connector support member comprises a notch that receives the mating edge of the base support member with the easel feature in the display configuration.

A fifth aspect of the present disclosure may include any of the first through fourth aspects, wherein the base support member comprises a notch that receives the connector support member with the easel feature in the display configuration.

A sixth aspect of the present disclosure may include any of the first through fifth aspects, wherein the envelope body, including the base support member and the connector support member, are formed from a single sheet of material.

A seventh aspect of the present disclosure may include any of the first through sixth aspects, wherein the material comprises cardboard, cardstock, paper, or combinations thereof.

An eighth aspect of the present disclosure may include any of the first through seventh aspects, wherein the base support member is adapted to pivot relative to a living hinge on the back of the envelope body.

A ninth aspect of the present disclosure may include any of the first through eighth aspects, wherein the base support member is adapted to pivot relative to a living hinge on the back of the envelope body.

A tenth aspect of the present disclosure may include any of the first through ninth aspects, wherein the envelope body comprises gap adjacent to at least one of the base support member and the connector support member.

An eleventh aspect of the present disclosure may include any of the first through tenth aspects, wherein the envelope body comprises at least two base support members.

A twelfth aspect of the present disclosure may include any of the first through eleventh aspects, wherein the base support member has a height that is between 20% and 80% the height of the envelope in a transverse direction.

A thirteenth aspect of the present disclosure may include any of the first through twelfth aspects, wherein the lines of separation is partially attached to the envelope body by one or more ticks.

A fourteenth aspect of the present disclosure may include any of the first through thirteenth aspects, wherein the envelope body further comprises a barrier sheet, wherein the barrier sheet is exposed with the easel feature in the display configuration.

A fifteenth aspect of the present disclosure may include any of the first through fourteenth aspects, wherein the envelope body encases scented materials.

According to a sixteenth aspect of the present disclosure, an envelope includes an envelope body having a first pair of substantially parallel edges that extend in a transverse direction and a second pair of substantially parallel edges that extend in a longitudinal direction, a face, and a back defining a pouch. The envelope includes a scented material that is located within the pouch. The envelope further includes a base support member partially detached from the envelope body along a line of separation and a connector support member partially detached from the envelope body along a line of separation. According to this embodiment, the connector support member is engaged with the base support member to form an easel feature in a display configuration.

A seventeenth aspect of the present disclosure may include the sixteenth aspect, wherein the connector support member engages a mating edge of the base support member with the easel feature in the display configuration.

An eighteenth aspect of the present disclosure may include the sixteenth aspect or the seventeenth aspect, wherein the connector support member comprises a notch that receives the mating edge of the base support member with the easel feature in the display configuration.

A nineteenth aspect of the present disclosure may include any of the sixteenth through eighteenth aspects, wherein the envelope body, including the base support member and the connector support member, are formed from a single sheet of material.

According to a twentieth aspect of the present disclosure, a method of displaying an envelope comprising an envelope body includes forming a base support member from a first region of the envelope body that is partially detachable from the envelope body along a line of separation and forming a connector support member from a second region of the envelope body that is partially detachable from the envelope body along a line of separation to form a connector support member. The envelope body has a first pair of substantially parallel edges that extend in a transverse direction and a second pair of substantially parallel edges that extend in a longitudinal direction, a face, and a back defining a pouch. The connector support member engages the base support member when the base support member is partially separated from the envelope body to form an easel feature.

A twenty first aspect of the present disclosure may include the twentieth aspect, wherein the first region of the envelope body extends into the second region of the envelope body providing the base support member with a support opening when the base support member is detached from the second region.

A twenty second aspect of the present disclosure may include the twentieth aspect or the twenty first aspect, wherein the connector support member engages a mating edge of the base support member with the easel feature in the display configuration.

A twenty third aspect of the present disclosure may include the twentieth through the twenty second aspects, wherein the connector support member comprises a notch that receives the mating edge of the base support member with the easel feature in the display configuration.

A twenty fourth aspect of the present disclosure may include the twentieth through the twenty third aspects, wherein the envelope body, including the base support member and the connector support member, are formed from a single sheet of material.

What is claimed is:

1. An envelope comprising:
    an envelope body having a first pair of substantially parallel edges that extend in a transverse direction and a second pair of substantially parallel edges that extend in a longitudinal direction, a face, and a back defining a pouch;
    a first region of the envelope body that is partially detachable from the envelope body along a line of separation to form a base support member;
    a second region of the envelope body that is partially detachable from the envelope body along a line of separation to form a connector support member;
    a closure flap located at one of the first pair of substantially parallel edges and folding portions extending outward at opposite sides of the closure flap, wherein the folding portions are folded along both of the one of the first pair parallel edges and the second pair of parallel edges forming a pair of safety folds along both of the second pair of parallel edges;
    wherein the connector support member engages the base support member when the base support member is partially separated from the envelope body to form an easel feature in a display configuration;
    wherein the first region of the envelope body is located between the pair of safety folds in the transverse direction and a bottom edge of the base support member is located inside a width of one of the folding portions in the transverse direction.

2. The envelope of claim 1, wherein the first region of the envelope body extends into the second region of the envelope body to provide the base support member with a support opening when the base support member is detached from the second region.

3. The envelope of claim 2, wherein the connector support member engages a mating edge of the base support member with the easel feature in the display configuration.

4. The envelope of claim 3, wherein the connector support member comprises a notch that receives the mating edge of the base support member with the easel feature in the display configuration.

5. The envelope of claim 3, wherein the base connector support member comprises a notch that receives the base support member with the easel feature in the display configuration.

6. The envelope of claim 1, wherein the envelope body, including the base support member and the connector support member, are formed from a single sheet of material.

7. The envelope of claim 6, wherein the base support member is adapted to pivot about a living hinge on the back of the envelope body.

8. The envelope of claim 1, wherein the base support member is adapted to pivot about a living hinge on the back of the envelope body.

9. The envelope of claim 1, wherein the envelope body comprises an access opening adjacent to at least one of the base support member and the connector support member.

10. The envelope of claim 1, wherein the envelope body comprises at least two base support members.

11. The envelope of claim 1, wherein the base support member has a height that is between 20% and 80% the height of the envelope in a transverse direction.

12. The envelope of claim 1, wherein the base support member is partially attached to the envelope body by one or more ticks.

13. The envelope of claim 1 further comprising a barrier sheet, wherein the barrier sheet is exposed with the easel feature in the display configuration.

14. The envelope of claim 1, wherein the envelope body encases scented materials.

15. An envelope comprising:
    an envelope body having a first pair of substantially parallel edges that extend in a transverse direction and a second pair of substantially parallel edges that extend in a longitudinal direction, a face, and a back defining a pouch;
    a scented material that is located within the pouch;
    a base support member partially detached from the envelope body along a line of separation;
    a connector support member partially detached from the envelope body along a line of separation; and
    a closure flap located at one of the first pair of substantially parallel edges and folding portions extending outward at opposite sides of the closure flap, wherein the folding portions are folded along both of the one of the first pair parallel edges and the second pair of parallel edges forming a pair of safety folds along both of the second pair of parallel edges;
    wherein the connector support member is engaged with the base support member to form an easel feature in a display configuration;
    wherein the base support member is located between the pair of safety folds in the transverse direction and a bottom edge of the base support member is located inside a width of one of the folding portions in the transverse direction with the envelope body in a flat, laid-out configuration before the base member is partially detached from the envelope body.

16. The envelope of claim 15, wherein the connector support member engages a mating edge of the base support member with the easel feature in the display configuration.

17. The envelope of claim 16, wherein the connector support member comprises a notch that receives the mating edge of the base support member with the easel feature in the display configuration.

18. A method of displaying an envelope comprising an envelope body, the method comprising:
   forming a base support member from a first region of the envelope body that is partially detachable from the envelope body along a line of separation; and
   forming a connector support member from a second region of the envelope body that is partially detachable from the envelope body along a line of separation to form a connector support member;
   wherein the envelope body has a first pair of substantially parallel edges that extend in a transverse direction, a second pair of substantially parallel edges that extend in a longitudinal direction, a face, and a back defining a pouch and a closure flap located at one of the first pair of substantially parallel edges and folding portions extending outward at opposite sides of the closure flap, wherein the folding portions are folded along both of the one of the first pair parallel edges and the second pair of parallel edges forming a pair of safety folds along both of the second pair of parallel edges; and
   the connector support member engaging the base member when the base support member is partially separated from the envelope body to form an easel feature in a display configuration;
   wherein a bottom edge of the base support member is located inside a width of one of the folding portions in the transverse direction with the envelope body in a flat, laid-out configuration before the base support member is partially detached from the envelope body.

19. The method of claim 18, wherein the first region of the envelope body extends into the second region of the envelope body providing the base support member with a support opening when the base support member is detached from the second region.

20. The method of claim 19, wherein the connector support member engaging a mating edge of the base support member with the easel feature in the display configuration.

* * * * *